United States Patent [19]

Floyd

[11] Patent Number: 5,925,809
[45] Date of Patent: Jul. 20, 1999

[54] SOYBEAN CULTIVAR CX339C

[75] Inventor: Thomas Lee Floyd, Bloomington, Ill.

[73] Assignee: Dekalb Genetics Corporation, DeKalb, Ill.

[21] Appl. No.: 08/839,171

[22] Filed: Apr. 23, 1997

Related U.S. Application Data

[51] Int. Cl.[6] .............................. A01H 1/02; A01H 5/00; A01H 5/04; C12N 5/10
[52] U.S. Cl. ......................... 800/312; 435/415; 435/426; 435/430; 800/260
[58] Field of Search .................................. 47/58, DIG. 1; 435/415, 426, 430; 800/200, 255, DIG. 26, 260, 312

[56] References Cited

U.S. PATENT DOCUMENTS

| | | | |
|---|---|---|---|
| 5,084,082 | 1/1992 | Sebastian | 71/90 |
| 5,304,728 | 4/1994 | Eby | 800/200 |
| 5,569,815 | 10/1996 | Eby | 800/200 |
| 5,576,474 | 11/1996 | Lussenden | 800/200 |
| 5,602,319 | 2/1997 | Rhodes et al. | 800/200 |

OTHER PUBLICATIONS

Allard, R.W., University of California, Davis, Calfornia. "Principles of Plant Breeding," Published by John Wiley & Sons, New York, University of Calfornia, Davis, California, pp. 50–98, 1960.

Fehr, "In: Soybeans: Improvement, Production and Uses," 2nd Edition, *Manograph* 16, p. 259, 1987.

Fehr, Walter R., Iowa State University. "Principles of Cultivar Development," vol. 1 Theory and Technique and vol. 2 Crop Species, Soybean pp. 533–376. Published by Macmillian Publishing Company, New York, 1987.

GRIN Database Entry PI438065 (Aug. 9, 1994), From The Internet http:/www.ars–grin.gov.

Sneep, J. and A.J.T. Hendriksen, eds., "Plant Breeding Perspectives," Wageningen: Centre for Agricultural Publishing and Documentation, 1979.

Nickell and Bernard, "Registration of L84–5873 and L84–5932 Soybean Germplasm Lines Resistant to Brown Stem Rot," *Crop Sci.*, 32:835, 1992.

Bernard, ed., "Evaluation of Maturity Groups I and II of the U.S.D.A. Soybean Collection," pp. 1–3, 58–59, Sep. 1966.

Bernard, ed., "Evaluation of Maturity Groups III and IV of the U.S.D.A. Soybean Collection," pp. 1–3, 5a–5d, 8a–8d, 9a–9d, 14a–14d, 17a–17d, 24a–24d, Apr. 1969.

1998 Seed Showcase for cultivar CX339c p.15.

*Primary Examiner*—Elizabeth F. McElwain
*Assistant Examiner*—Amy J. Nelson
*Attorney, Agent, or Firm*—Arnold White & Durkee

[57] ABSTRACT

The novel soybean cultivar, designated CX339c, is disclosed. The invention relates to the seeds of soybean cultivar CX339c, to the plants of soybean CX339c and to methods for producing a soybean plant produced by crossing the cultivar CX339c with itself or another soybean variety. The invention further relates to hybrid soybean seeds and plants produced by crossing the cultivar CX339c with another soybean cultivar.

14 Claims, No Drawings

SOYBEAN CULTIVAR CX339C

BACKGROUND OF THE INVENTION

The present invention relates to the new and distinctive soybean cultivar, designated CX339c. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for generally three or more years. The best lines are candidates for new commercial cultivars; those still deficient in a few traits may be used as parents to produce new populations for further selection.

These processes, which lead to the final step of marketing and distribution, may take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to one or more widely grown standard cultivars. Single observations are generally inconclusive, replicated observations provide a better estimate of its genetic worth.

The goal of plant breeding is to develop new, unique and superior soybean cultivars and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same soybean traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new soybean cultivars.

The development of new soybean cultivars requires the development and selection of soybean varieties, the crossing of these varieties and selection of superior hybrid crosses. The hybrid seed is produced by manual crosses between selected male-fertile parents or by using male sterility systems. These hybrids are selected for certain single gene traits such as pod color, flower color, pubescence color or herbicide resistance which indicate that the seed is truly a hybrid. Additional data on parental lines as well as the phenotype of the hybrid influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$'s. Selection of the best individuals may begin in the $F_2$ population; then, beginning in the $F_3$, the best individuals in the best families can be selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self-or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor or nonreccurent parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Soybean, Glycine max (L), is an important and valuable field crop. Thus, a continuing goal of plant breeders is to develop stable, high yielding soybean cultivars that are agronomically sound. The reasons for this goal are obviously to maximize the amount of grain produced on the land used and to supply food for both animals and humans. To accomplish this Goal, the soybean breeder must select and develop soybean plants that have the traits that result in superior cultivars.

SUMMARY OF THE INVENTION

According to the invention, there is provided the novel soybean cultivar, designated, CX339c. This invention thus relates to the seeds of soybean cultivar CX339c, to the plants of soybean CX339c and to methods for producing a soybean plant produced by crossing the soybean CX339c with itself or another soybean line.

The current invention is, therefore, directed to methods for producing a soybean plant by crossing a first parent soybean plant with a second parent soybean plant, wherein the first or second soybean plant is a soybean plant from the line CX339c. Further, both first and second parent soybean plants may be from the cultivar CX339c. Therefore, any methods using the cultivar CX339c is part of this invention including: selfing, backcrosses, hybrid breeding, and crosses to populations. Any plants produced using cultivar CX339c as a parent are within the scope of this invention. As used herein, the term "plant" includes plant cells, plant protoplasts, plant cells of tissue culture from which soybean plants can be regenerated, plant calli, plant clumps, and plant cells that are intact in plants or parts of plants, such as pollen, flowers, seeds, pods, leaves, stems, and the like.

DEFINITIONS

In the description and tables which follow, a number of terms are used. In order to provide a clear and consistent understanding of the specification and claims, including the scope to be given such terms, the following definitions are provided:

Maturity Date. Plants are considered mature when 95% of the pods have reached their mature color. The maturity date is typically described in measured days from January first, which may be referred to as "Julian Days".

Seed Yield (Bushels/Acre). The yield in bushels/acre is the actual yield of the grain at harvest.

Lodging Resistance. Lodging is rated on a scale of 1 to 9. A score of 1 indicates erect plants. A score of 5 indicates plants are leaning at a 45 degree(s) angle in relation to the ground and a score of 9 indicates plants are laying on the ground.

Phytophthora Tolerance. Tolerance to Phytophthora root rot is rated on a scale of 1 to 9, with a score of 1 being the best or highest tolerance ranging down to a score of 9, which indicates the plants have no tolerance to Phytophthora.

Emergence. This score indicates the ability of the seed to emerge from the soil after planting. Each genotype is given a 1 to 9 score based on its percent of emergence. A score of 1 indicates an excellent rate and percent of emergence, an intermediate score of 5 indicates average ratings and a 9 score indicates a very poor rate and percent of emergence.

Iron-Deficiency Chlorosis. Plants are scored 1 to 9 based on visual observations. A score of 1 means no stunting of the plants or yellowing of the leaves and a score of 9 indicates the plants are dead or dying caused by iron-deficiency chlorosis, a score of 5 means plants have intermediate health with some leaf yellowing.

Brown Stem Rot. This is a visual disease score from 1 to 9 comparing all genotypes in a given test. The score is based on leaf symptoms of yellowing and necrosis caused by brown stem rot. A score of 1 indicates no symptoms. Visual scores range to a score of 9 which indicates severe symptoms of leaf yellowing and necrosis.

Shattering. The amount of pod dehiscence prior to harvest. Pod dehiscence involves seeds falling from the pods to the soil. This is a visual score from 1 to 9 comparing all genotypes within a given test. A score of 1 means pods have not opened and no seeds have fallen out. A score of 5 indicates approximately 50% of the pods have opened, with seeds falling to the ground and a score of 9 indicates 100% of the pods are opened.

Plant Height. Plant height is taken from the top of soil to the top node of the plant and is measured in inches.

DETAILED DESCRIPTION OF THE INVENTION

When the term soybean variety is used in the context of the present invention, this also includes any single gene or multiple gene conversions of that soybean variety. The terms single gene or multiple gene converted plant, as used herein, refers to those soybean plants which are developed by the plant breeding technique of backcrossing. Through backcrossing, essentially all of the desired morphological and physiological characteristics of a variety may be recovered in addition to the gene or genes transferred into the variety via the backcrossing technique. Backcrossing methods can be used with the present invention to improve or introduce one or more characteristics into the current soybean variety. The term backcrossing as used herein refers to the repeated crossing of a hybrid progeny back to one of the parental soybean plants for that variety. The parental soybean plant which contributes the gene(s) for the desired characteristic(s) is termed the nonrecurrent or donor parent. This terminology refers to the fact that the nonrecurrent parent is used one time in the backcross protocol and therefore does not recur. The parental soybean plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a soybean plant is obtained wherein essentially all of the desired morphological and physiological characteristics of the recurrent parent are recovered in the converted plant, in addition to the transferred gene(s) from the nonrecurrent parent. The process may be carried out as many times as desired, using either the same or another nonrecurrent parent, to introduce multiple traits into CX339c.

The selection of a suitable recurrent parent is an important step for a successful backcrossing procedure. The goal of a backcross protocol is to alter or substitute a particular trait or characteristic in the original inbred. To accomplish this, one or more traits of the recurrent variety is modified or substituted with the desired gene from the nonrecurrent parent. Thereby, while retaining essentially all of the desired genetic background of the recurrent parent, and therefore the desired agronomic characteristics, one or more desirable traits from the nonrecurrent parent(s) are added. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristics has been successfully transferred.

Many single gene traits have been identified that are not regularly selected for in the development of a new inbred but that can be improved by backcrossing techniques. Single gene traits may or may not be transgenic. Examples of these traits are bacterial, fungal, or viral disease resistance, insect resistance, male fertility, enhanced nutritional quality, industrial usage, yield stability or yield enhancement. These genes are generally inherited through the nucleus.

Direct selection may be applied where the single gene acts as a dominant trait. For example, one may select for a herbicide resistance trait. For the selection process, the progeny of an initial cross are sprayed with the herbicide prior to the backcrossing. The herbicide eliminates any plants which do not have the desired herbicide resistance characteristic, and thus only those plants which have the herbicide resistance gene will be used in the subsequent backcross. This process is then repeated for all additional generations.

Flower color is an example of a recessive trait. In this example, the progeny resulting from the first backcross generation ($BC_1$) are grown and selfed. The selfed progeny from the $BC_1$ plant are grown to determine which $BC_1$ plants carry the recessive gene for flower color. In other recessive traits, additional progeny testing, for example growing additional generations such as the $BC_1F_2$ may be required to determine which plants carry the recessive gene.

Selection of soybean plants for breeding is not necessarily dependent on the phenotype of a plant and instead can be based on genetic investigations. For example, one may find a suitable genetic marker, such as a restriction fragment length polymorphism, which is closely genetically linked to a trait of interest. This marker may therefore be used to identify the presence or absence of a trait in the offspring of a particular cross, and hence may be used in selection of progeny for continued breeding. This technique may commonly be referred to as marker assisted selection. Any other type of genetic or other assay which is able to identify the relative presence or absence of a trait of interest in a plant may be also be useful for breeding purposes. Exemplary procedures of such are well known in the art and are disclosed in U.S. patent appl. Ser. No. 08/113,561, filed Aug. 25, 1993, which is specifically incorporated herein by reference. Such methods will be of particular utility in the case of recessive traits and variable phenotypes, or where conventional assays are expensive, time consuming or otherwise disadvantageous.

When used in conjunction with the word "comprising" or other open language in the claims, the words "a" and "an" denote "one or more".

Variety Description Information

Soybean cultivar CX339c has superior characteristics and is an $F_4$ plant selection from the cross CX340c x CX469c. CX339c was developed as follows:

| | |
|---|---|
| Summer 1989 | The cross CX340c x CX469c was made. |
| Winter 1989 | $F_1$ generation was grown (range 1, row 67). $F_2$ generation was grown (range 67, rows 1–17). |
| Summer 1990 | $F_3$ generation was grown (range 432, row 25 through range 433, row 20). |
| Summer 1991 | $F_4$ generation was grown (range 460, row 1 through range 481, row 40). |
| Summer 1992 | $F_5$ generation was grown (range 326, row 38 through range 347, row 6). Range 330, row 40 was selected. |
| Summer 1993 | $F_6$ generation was grown. |
| Summer 1994 | $F_7$ generation was grown and 125 pounds of seed was produced. |

-continued

| | | |
|---|---|---|
| Summer 1995 | $F_8$ generation was grown and 57 bushels of breeder seed was produced. | |
| Winter 1995 | $F_9$ generation was grown. | |
| Summer 1996 | $F_{10}$ generation was grown and seed was increased. | |

The results of an objective description of the variety, based on data collected at Bloomington, IL, were as follows:

| | | |
|---|---|---|
| 1. SEED SHAPE: | | Spherical |
| 2. SEED COAT COLOR: (Mature Seed) | | Yellow |
| 3. SEED COAT LUSTER: (Mature Hand Shelled Seed) | | Dull |
| 4. SEED SIZE: (Mature Seed) | | 17.0 Grams per 100 seeds |
| 5. HILUM COLOR: (Mature Seed) | | Black |
| 6. COTYLEDON COLOR: (Mature Seed) | | Yellow |
| 7. SEED PROTEIN PEROXIDASE ACTIVITY: | | High |
| 8. SEED PROTEIN ELECTROPHORETIC BAND: | | |
| 9. HYPOCOTYL COLOR: | | Green with bronze below cotyleodons |
| 10. LEAFLET SHAPE: | | Ovate |
| 11. LEAFLET SIZE: | | Medium |
| 12. LEAF COLOR: | | Medium Green |
| 13. FLOWER COLOR: | | White |
| 14. POD COLOR: | | Tan |
| 15. PLANT PUBESCENCE COLOR: | | Tawny |
| 16. PLANT TYPE: | | Medium bush |
| 17. PLANT HABIT: | | Indeterminate |
| 18. MATURITY GROUP: | | III |
| 19. DISEASE REACTION: | | |
| (0 = Not Tested; 1 = Susceptible; 2 = Resistant) | | |
| Bacterial Diseases: | Fungal Diseases: | |
| Bacterial Pustule: 0 | Brown Spot: | 0 |
| Bacterial Blight: 0 | Frogeye Leaf Spot: | 0 |
| Wildfire: 0 | Target Spot: | 0 |
| | Downy Mildew: | 0 |
| Viral Diseases: | Powdery Mildew: | 0 |
| Bud Blight: 0 | Brown Stem Rot: | Resistant* |
| Yellow Mosaic: 0 | Stem Canker: | 0 |
| Cowpea Mosaic: 0 | Pod and Stem Blight: | 0 |
| Pod Mottle: 0 | Purple Seed Strain: | 0 |
| Seed Mottle: 0 | Rhizoctonia Root Rot: | 0 |
| | Sudden Death Syndrome Phytophthora Rot: | Resistant* |
| Nematode Diseases: | Races 1–9: | 0 |
| Soybean Cyst Nematode: | | |
| Race(s): 3    2 | | |
| Lance Nematode: 0 | | |
| Southern Root Knot Nematode: 0 | | |
| Northern Root Knot Nematode: 0 | *the score for Brown Stem Rot and Sudden Death Syndrome is 1 (on a 1–9 scale; 1 = most resistant). | |
| Peanut Root Knot Nematode: 0 | | |
| Reniform Nematode: 0 | | |
| Other: | | |
| 20. PHYSIOLOGICAL RESPONSES: | | |
| (0 = Not Tested; 1 = Susceptible; 2 = Resistant) | | |
| Iron Chlorosis on Calcareous Soil: 0 | | |
| Other: 0 | | |
| 21. INSECT REACTION: | | |
| (0 = Not Tested; 1 = Susceptible; 2 = Resistant) | | |
| Mexican Bean Beetle: 0 | | |
| Potato Leaf Hopper: 0 | | |
| Other: 0 | | |

Soybean variety CX339c has been judged to be uniform for breeding purposes and testing after five generations of selfing. CX339c was reproduced and judged uniform and stable for an additional five generations. Variety CX339c shows no variants other than what would normally be expected due to environment or that would occur for almost any characteristic during the course of repeated sexual reproduction. Some of the criteria used to select in various generations include: seed yield, lodging resistance, emergence, seedling vigor, disease tolerance, maturity, plant height and shattering resistance.

The inventors believe that CX339c is most similar to soybean variety CX469c (PVP No. 9000006); however, CX469c is a mid Group IV variety whereas CX339c is a mid Group III variety. CX339c also differs from its parental varieties, CX340c and CX469c. It is significantly higher yielding than CX340c (2.6 bushels per acre), although it does not differ in significantly from CX340c in routinely measured morphological traits. Based on interpolation of the estimated maturities of each variety, CX339c is estimated to be 13 days earlier in maturity than CX469c. CX339c also has white flowers while CX469c has purple flowers.

Variety Comparison

Direct comparisons were made between CX339c and competing commercial varieties. Traits measured were yield, maturity, and lodging. The results of the comparison are given in Tables 1–3. In Table 1, column 1 gives the competitor variety, columns 2, 3, and 4 give the yield in bushels per acre of CX339c, the competitor variety and the difference, respectively. Column 5 shows the number of observations in each difference and column 6 shows the probability associated with each difference. In Table 2, column 1 shows the Competitor Variety, and columns 2, 3, and 4 show the maturity of CX339c, the competitor variety and the difference, respectively. Column 5 shows the number of observations in each difference and column 6 shows the probability associated with each difference. In Table 3, column 1 shows the competitor variety and Columns 2, 3, and 4 show the lodging of CX339c, the competitor variety and the difference, respectively. Column 5 shows the number of observations in each difference and column 6 shows the probability associated with each difference.

TABLE 1

Yield comparison of CX339c and competing varieties.

| Competitor Variety | CX339c YIELD | Competitor YIELD | YIELD Difference | Number of Observations | P-value |
|---|---|---|---|---|---|
| ASGA3237 | 51.8 | 49.4 | 2.4 | 32 | 0.040 |
| ASGA3304 | 51.3 | 49.0 | 2.2 | 27 | 0.060 |
| ASGA3431 | 53.1 | 52.5 | 0.6 | 70 | 0.478 |
| CX289 | 54.7 | 50.8 | 3.9 | 25 | 0.012 |
| CX297 | 51.1 | 44.9 | 6.3 | 19 | 0.000 |
| CX313 | 54.2 | 52.0 | 2.2 | 85 | 0.001 |
| CX314 | 52.0 | 49.3 | 2.7 | 23 | 0.039 |
| CX340C | 54.3 | 51.7 | 2.6 | 89 | 0.000 |
| CX351 | 52.1 | 48.7 | 3.3 | 38 | 0.001 |
| CX360 | 51.9 | 49.1 | 2.8 | 32 | 0.030 |
| CX366 | 56.3 | 51.0 | 5.3 | 30 | 0.000 |
| CX368 | 52.1 | 48.1 | 4.0 | 31 | 0.000 |
| CX375 | 51.3 | 49.2 | 2.0 | 25 | 0.061 |
| CX377 | 52.0 | 48.9 | 3.1 | 46 | 0.001 |
| CX394C | 54.5 | 50.0 | 4.4 | 41 | 0.000 |
| CX399 | 54.5 | 52.1 | 2.4 | 41 | 0.036 |
| CX404 | 59.6 | 56.0 | 3.6 | 18 | 0.036 |
| GUTW334 | 50.2 | 47.6 | 2.6 | 13 | 0.050 |
| PION9392 | 52.2 | 52.1 | 0.1 | 14 | 0.957 |

TABLE 2

Maturity comparison of CX339c and competing varieties.

| Competitor Variety | CX339c MATUR | Competitor MATUR | MATUR Difference | Number of Observations | P-value |
|---|---|---|---|---|---|
| ASGA3237 | 272.8 | 272.8 | 0.0 | 10 | 1.000 |
| ASGA3304 | 272.4 | 273.6 | −1.2 | 10 | 0.126 |
| ASGA3431 | 275.5 | 275.6 | −0.1 | 23 | 0.875 |
| CX289 | 277.8 | 273.7 | 4.2 | 9 | 0.000 |
| CX297 | 273.4 | 269.0 | 4.4 | 10 | 0.000 |
| CX313 | 274.2 | 272.6 | 1.6 | 26 | 0.000 |
| CX314 | 273.3 | 272.3 | 1.0 | 13 | 0.134 |
| CX340C | 274.1 | 274.8 | −0.7 | 29 | 0.054 |
| CX351 | 274.8 | 275.1 | −0.4 | 14 | 0.222 |
| CX360 | 274.5 | 275.0 | −0.6 | 14 | 0.263 |
| CX366 | 268.8 | 269.3 | −0.6 | 12 | 0.407 |
| CX368 | 274.5 | 275.2 | −0.7 | 14 | 0.065 |
| CX375 | 272.4 | 274.5 | −2.1 | 10 | 0.033 |
| CX377 | 274.1 | 275.3 | −1.2 | 14 | 0.020 |
| CX394C | 270.4 | 273.1 | −2.7 | 13 | 0.000 |
| CX399 | 270.4 | 273.5 | −3.1 | 13 | 0.000 |
| CX404 | 268.3 | 271.7 | −3.3 | 6 | 0.000 |
| GUTW334 | 269.2 | 272.5 | −3.3 | 6 | 0.042 |
| PION9392 | — | — | — | — | — |

TABLE 3

Lodging comparison of CX339c and competing varieties.

| Competitor Variety | CX339c LODGE | Competitor LODGE | LODGE Difference | Number of Observations | P-value |
|---|---|---|---|---|---|
| ASGA3237 | — | — | — | — | — |
| ASGA3304 | — | — | — | — | — |
| ASGA3431 | 2.3 | 2.3 | 0.0 | 9 | 1.000 |
| CX289 | 2.5 | 2.6 | −0.1 | 6 | 0.611 |
| CX297 | 2.7 | 3.6 | −0.9 | 6 | 0.186 |
| CX313 | 2.6 | 2.7 | −0.1 | 14 | 0.797 |
| CX314 | 2.7 | 2.4 | 0.3 | 6 | 0.542 |
| CX340C | 2.6 | 2.6 | 0.0 | 14 | 1.000 |
| CX351 | 2.4 | 2.6 | −0.2 | 7 | 0.448 |
| CX360 | 2.7 | 3.0 | −0.3 | 6 | 0.394 |
| CX366 | 3.2 | 3.8 | −0.7 | 6 | 0.102 |
| CX368 | 2.7 | 2.5 | 0.2 | 6 | 0.679 |
| CX375 | — | — | — | — | — |
| CX377 | — | — | — | — | — |
| CX394C | 3.0 | 2.4 | 0.6 | 7 | 0.172 |
| CX399 | 3.0 | 2.9 | 0.1 | 7 | 0.766 |
| CX404 | — | — | — | — | — |
| GUTW334 | — | — | — | — | — |
| PION9392 | — | — | — | — | — |

Deposit Information

A deposit of the DEKALB Genetics propriety soybean cultivar CX339c, disclosed above and recited in the appended claims, has been made with the American Type Culture Collection (ATCC), 10801 University Blvd., Manassas, Virginia, on Sep. 8, 1998. All restrictions upon the deposit have been removed, and the deposit is intended to meet all of the requirements of 37 C.F.R. §1.801–1.809. The ATCC accession number is ATCC 203187. The deposit will be maintained in the depository for a period of 30 years, or 5 years after the last request, or for the effective life of the patent, whichever is longer, and will be replaced as necessary during that period.

REFERENCES

The following references, to the extent that they provide exemplary procedural or other details supplementary to those set forth herein, are specifically incorporated herein by reference.

U.S. patent appl. Ser. No. 08/113,561
U.S. Pat. No. 5,304,728
Evaluation of Maturity Groups III and IV of the USDA Soybean Collection, 1969, Compiled by
R. L. Bernard, p.p. 1–3, 5a–5d, 8a–8d, 9a–9d, 14a–14d, 17a–17d, 24a–24d, and 25a–25d.
Evaluation of Maturity Group I and II, USDA Soybean Collection, 1966, pp.1,58–59. Fehr, "In: Soybeans: Improvement, Production and Uses," 2nd Edition, Monograph 16, p.259, 1987.
GRIN Database Entry P1438065 (Aug. 9, 1994).
Illinois Agric. Exper. Station Release, Lines 84–5873 and 84–5932, 1991.

What is claimed is:

1. Soybean seed designated CX339c, a sample of said seed having been deposited under ATCC Accession No. 203187.

2. A plant or plants of the soybean cultivar designated CX339c produced by growing the seed of claim 1.

3. Pollen of the plant of claim 2.

4. An ovule or ovules of the plant of claim 2.

5. A soybean plant with all of the physiological and morphological characteristics of the soybean plant of claim 2.

6. A tissue culture of the plant of claim 2.

7. A soybean plant regenerated from the tissue culture of claim 6, wherein the regenerated soybean plant has all of the physiological and morphological characteristics of a plant grown from a soybean seed designated CX339c, a sample of said soybean seed designated CX339c having been deposited under ATCC Accession No. 203187.

8. A soybean plant obtained from the soybean plant of claim 2 by a single gene conversion.

9. A soybean plant obtained from the soybean plant of claim 2 by two single gene conversions.

10. A method of producing soybean seeds comprising:
   a) planting seeds of soybean cultivar CX339c, a sample of said seeds of soybean cultivar CX339c having been deposited under ATCC Accession No. 203187;
   b) growing soybean plants from said seeds until said plants bear flowers;
   c) fertilizing the flowers of said plants; and,
   d) harvesting seeds produced from said plants.

11. A method of producing hybrid soybean seeds comprising the steps of:
   a) planting seeds of soybean cultivar CX339c, a sample of said seeds of soybean cultivar CX339c having been deposited under ATCC Accession No. 203187, and of another soybean cultivar;
   b) growing soybean plants from said seeds until said plants bear flowers;
   c) emasculating flowers of either cultivar;
   d) cross pollinating said flowers; and
   e) harvesting seeds resulting from said cross pollinating.

12. A method of producing hybrid soybean seeds comprising the steps of:
   a) planting seeds of soybean cultivar CX339c, a sample of said seeds of soybean cultivar CX339c having been deposited under ATCC Accession No. 203187, and of another soybean cultivar;
   b) growing soybean plants from said seeds until said plants bear flowers;
   c) cross pollinating said flowers prior to pollen shed; and
   d) harvesting seeds resulting from said cross pollinating.

13. A first generation ($F_1$) hybrid soybean plant produced by crossing the plant of claim 2 with a second distinct soybean plant.

14. Seeds of the first generation $F_1$ hybrid soybean plant of claim 13.

* * * * *